United States Patent [19]

Harbridge

[11] Patent Number: 4,622,177
[45] Date of Patent: Nov. 11, 1986

[54] 9-DEOXY-9-ISOCYANATO CLAVULANTE INTERMEDIATES

[75] Inventor: John B. Harbridge, Redhill, England

[73] Assignee: Beecham Group p.l.c., United Kingdom

[21] Appl. No.: 530,752

[22] Filed: Sep. 9, 1983

[30] Foreign Application Priority Data

Sep. 11, 1982 [GB] United Kingdom ................ 8225989

[51] Int. Cl.⁴ .......................................... C07D 487/04
[52] U.S. Cl. .................................................... 540/348
[58] Field of Search ..................................... 260/245.3

[56] References Cited

FOREIGN PATENT DOCUMENTS 55062 6/1982 European Pat. Off. .
68609 1/1983 European Pat. Off. .

Primary Examiner—Mark L. Berch
Attorney, Agent, or Firm—Hopgood, Calimafde, Kalil, Blaustein & Judlowe

[57] ABSTRACT

A compound of formula I

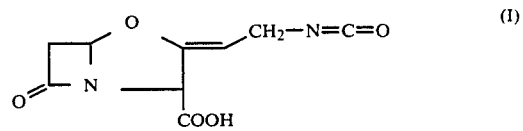

or a salt or ester thereof.

Processes for the preparation of these compounds and the use of these compounds in the preparation of further bicyclic compounds are also disclosed.

4 Claims, No Drawings

9-DEOXY-9-ISOCYANATO CLAVULANTE INTERMEDIATES

This invention relates to novel β-lactam compounds, processes for their preparation and the their use as chemical intermediates.

Derivatives of clavulanic acid of formula (A), and its salts and esters are disclosed in U.K. patent specification Nos. 1 508 977 and 1 508 978.

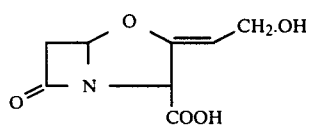

According to the present invention there is provided a compound of formula (I):

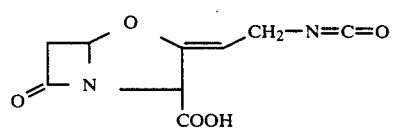

or a salt or ester thereof.

The compound of formula (I) or salts or esters thereof are useful as chemical intermediates in, for example, the preparation of pharmocologically active derivatives of clavulanic acid. Therefore, the salts or esters of the compound of formula (I) are preferably pharmaceutically acceptable although non-pharmaceutically acceptable salts and esters are within the ambit of this invention since they are useful intermediates to both the pharmaceutically acceptable salts and pharmaceutically acceptable esters of the compound of formula (I) and to non-pharmaceutically acceptable salts and esters of other derivatives of clavulanic acid.

Preferably the compound of formula (I) is in the form of an ester.

Suitable esters of the compound of formula (I) include those cleavable by biological methods such as enzymatic hydrolysis and in-vivo hydrolysis, and those cleavable by chemical methods such as hydrogenolysis, hydrolysis, electrolysis and photolysis.

Suitably, the carboxylic acid group of formula (I) is esterified by a group of sub-formula (a), (b), (c), (d), (e) or (f):

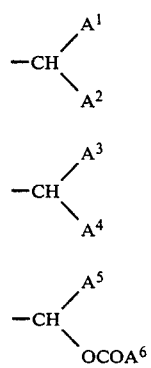

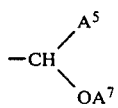

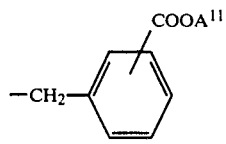

wherein:

$A^1$ is a hydrogen atom, $C_{1-6}$ alkanoyl or a $C_{1-5}$ alkyl group optionally substituted by $C_{1-7}$ alkoxy or $C_{1-7}$ carboxylic acyloxy, or an alkenyl or alkynyl group of up to 5 carbon atoms;

$A^2$ is a hydrogen atom or a methyl group; or $CHA^1A^2$ is a phenacyl or bromophenacyl group;

$A^3$ is a phenyl group, or a phenyl group substituted by a fluorine, chlorine or bromine atom or a nitro, $C_{1-3}$ alkyl or $C_{1-3}$ alkoxy group;

$A^4$ is a hydrogen atom or a phenyl group, or a phenyl group substituted by a fluorine, chlorine or bromine atom or a nitro, $C_{1-3}$ alkyl or $C_{1-3}$ alkoxy group;

$A^5$ is a hydrogen atom or a methyl group;

$A^6$ is a $C_{1-4}$ alkyl, phenyl or $C_{1-4}$ alkoxy group, or $A^5$ is joined to $A^6$ to form a phthalidyl, dimethylphthalidyl or dimethoxyphthalidyl group;

$A^7$ is a $C_{1-4}$ alkyl, phenyl, chlorphenyl or nitrophenyl group;

$A^8$ is a $C_{1-4}$ alkyl or phenyl group;

$A^9$ is a $C_{1-4}$ alkyl or phenyl group;

$A^{10}$ is $C_{1-4}$ alkyl; and $A^{11}$ is $C_{1-4}$ alkyl.

Favourably, $A^1$ is a hydrogen atom or a methyl, ethyl, vinyl, or ethenyl group. Favourably, $A^2$ is a hydrogen atom. Favourably, $A^3$ is a phenyl, p-bromophenyl, p-methoxyphenyl or p-nitrophenyl group. Favourably, $A^4$ is a hydrogen atom. Favourably, $A^6$ is a methyl, t-butyl or ethoxy group, or is joined to $A^5$. Favourably, $A^7$ is a methyl group.

Preferred groups of sub-formula (a) include the methyl, ethyl and acetonyl groups.

Preferred groups of sub-formula (b) include the benzyl and p-nitrobenzyl groups.

Preferred groups of sub-formula (c) include the acetoxymethyl, pivaloyloxymethyl, α-ethoxycarbonyloxymethyl and phthalidyl groups.

A preferred group of sub-formula (d) is the methoxymethyl group.

Preferred groups of sub-formula (e) include the triisopropylsilyl, tert-butyldimethylsilyl and tertbutyldiphenylsilyl groups.

A preferred group of sub-formula (f) is p-methoxycarbonylbenzyl.

Particularly preferred esterifying groups are the benzyl, p-nitrobenzyl and phthalidyl groups.

Pharmaceutically acceptable in-vivo hydrolysable esters are those esters which hydrolyse in the human body to produce the parent acid or its salt. Such esters may be identified by administration to a test animal such as a rat or mouse by intravenous administration and thereafter examining the test animals's body fluids for the presence of the compound of the formula (I) or its salt. Suitable esters of this type include those of sub-formula (c) as defined above.

This invention also provides a process for the preparation of compound of formula (I), or a salt or ester thereof which process comprises reacting a compound of formula (II):

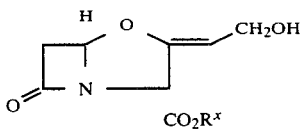 (II)

wherein $R^x$ is a carboxy-protecting group with
(i) isocyanic acid;
(ii) a compound of formula (III):

 (III)

wherein $R^1$ and $R^2$ are each independently $C_{1-6}$ alkyl, aryl or aryl($C_{1-6}$)alkyl; and
(iii) a compound of formula (IV):

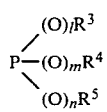 (IV)

wherein l, m and n are each independently 0 or 1, and $R^3$, $R^4$ and $R^5$ are each independently $C_{1-6}$ alkyl, aryl or aryl($C_{1-6}$)alkyl;
and thereafter, where necessary, carrying out one or more of the following steps:
(a) removing the carboxy-protecting group $R^x$; and/or
(b) converting a salt to the free carboxylic acid of formula (I) or to an ester, or to a different salt.

Isocyanic acid is sometimes known as cyanic acid due to the probable existance of tautomers i.e.:

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$)alkyl, hydroxy, amino, nitro, carboxy, $C_{1-6}$ alkoxycarbonyl, $C_{1-6}$ alkoxycarbonyl-($C_{1-6}$)-alkyl $C_{1-6}$ alkylcarbonyloxy, or $C_{1-6}$ alkycarbonyl groups.

Suitable compounds of formula (III) include those wherein $R^1$ and $R^2$ are each independently methyl, ethyl, propyl, butyl, phenyl or benzyl. It is generally convenient that $R^1$ and $R^2$ represent the same moiety. Particularly suitable compounds of the formula (III) include those wherein $R^1$ and $R^2$ each represent ethyl, t-butyl or isopropyl.

Suitable compounds of formula (IV) include those wherein $R^3$, $R^4$ and $R^5$ are each independently methyl, ethyl, n-propyl, n-butyl, benzyl, phenyl or methoxyphenyl. It is generally convenient that $R^3$, $R^4$ and $R^5$ each represent the same moiety. Favoured compounds of formula (IV) include tri-arylphosphines and tri-alkylphosphites. Particularly suitable compounds of formula (IV) include triphenylphosphine and tri-p-methoxyphenylphosphine, but especially triphenyl-phosphine.

Suitable carboxy-protecting groups for the group $-CO_2R^x$ in formula (II) include ester derivatives of the carboxylic acid. The derivative is preferably one which may readily be cleaved at a later stage of the reaction.

Suitable ester-forming carboxy-protecting groups are those which may be removed under conventional conditions. Such groups for $R^x$ include benzyl, p-methoxybenzyl, 2,4,6-trimethybenzyl, 3,5-di-t-butyl-benzyl, 4-pyridylmethyl, allyl, diphenylmethyl, triphenymethyl, 2-benzyloxyphenyl, 4-methylthiophenyl, methoxymethyl, a silyl or a phosphorus-V-containing group, or methyl or ethyl, but especially benzyl.

The free carboxylic acid or a salt thereof may be regenerated from any of the above esters by usual methods appropriate to the particular $R^x$ group; for example, by base-catalysed hydrolysis, by enzymically-catalysed hydrolysis or by hydrogenation.

The preceding reaction normally takes place in a solvent inert under the reaction conditions such as toluene, dichloromethane, tetrahydrofuran or dioxane. For example, a solution of the isocyanic acid may be prepared by extraction of a cooled, acidified solution of an alkali metal cyanate (such as potassium or sodium cyanate) with an immiscible solvent, or by distillation of isocyanic acid into a suitable solvent (such as tetrahydrofuran) which allows the preparation of a more concentrated but less stable solution.

The reaction is generally carried out at a depressed or non-elevated temperature, for exaple $-80°$ to $+30°$ C., and preferably at a depressed temperature, for example $-40°$ to $0°$ C., and conveniently at about $-10°$ C.

Preferably, the compounds of formulae (III) and (IV) are not mixed together with the compound of formula (II) in the absence of nucleophile. More preferably, the compound of formula (III) is added rapidly to the reaction mixture as the last ingredient.

The compound of formula (I) and salts and particularly the esters thereof may be used as a chemical intermediate or starting material, for example, in reactions known in the art to be typical of isocyanates such as those described in the Chemistry of Cyanates and their Thio Derivatives (Part 2), Edited by Saul Patai, Published by John Wiley & Sons (1977).

Further according to the present invention there is provided a process for the preparation of a compound of formula XI

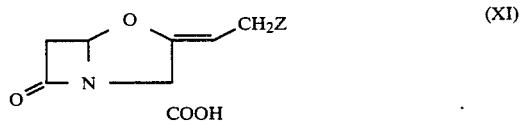 (XI)

or a salt or ester thereof, wherein Z is a group $NHCOOR^6$, $NHCXR^7$ or $NH_2$ wherein $R^6$ is optionally substituted $C_{1-6}$ alkyl, $C_{2-6}$ alkenyl, aryl, aryl($C_{1-6}$)alkyl; X is oxygen or sulphur and $R^7$ is hydrogen, an aliphatic group, a cycloaliphatic group, an aryl group or a C-attached heterocyclic group, by reaction of a compound of formula (IA)

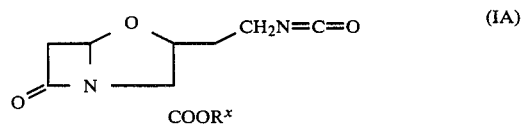 (IA)

where $R^x$ is a carboxy blocking group with a compound of formula (VI) or (VIII)

   (VI)

   (VIII)

or equivalent amounts of water respectively, wherein $R^6$, $R^7$ and X are as hereinbefore defined and $X^1$ is oxygen or sulphur; and thereafter if desired:

(a) removing the carboxy protecting group $R^x$;
(b) converting a salt to the free carboxylic acid or to an ester or to a different salt.

Suitable carboxy-blocking groups $R^x$ are those defined previously in relation to formula II.

For example, an ester compound of formula (I) may be used to prepare an ester compound of formula (V) which are disclosed in U.K. patent specification Nos. 1 603 208 and 1 594 934;

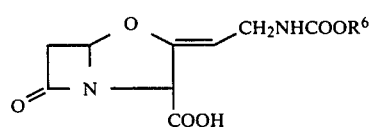   (V)

wherein $R^6$ is optionally substituted $C_{1-6}$ alkyl, $C_{2-6}$ alkenyl, aryl, aryl($C_{1-6}$)alkyl, by reaction with an alcohol of formula (VI):

   (VI)

wherein $R^6$ is as defined in relation to formula (V).

Preferably, $R^6$ is aryl($C_{1-6}$)alkyl such as benzyl, or $C_{1-6}$ alkyl substituted with tri($C_{1-6}$)alkylsilyl, such as 2-trimethylsilyl ethyl.

It is not necessary to isolate the ester of the compound of formula (I) in this reaction or any of the following reactions; instead, the alcohol of formula (VI) may be added in situ as this reaction can be carried out under the same conditions as the preparation of an ester of the compound of formula (I). The compound of formula (VI) will, of course, not be added to the reaction mixture until the preparation of the ester of the compound of formula (I) is effected.

If the ester of the compound of formula (I) is isolated, the compound of formula (V) may be prepared by dissolving the compound of formula (I) in excess alcohol of formula (VI) or by dissolving it in a solvent such as ethyl acetate and adding the alcohol and, after the reaction has taken place, removing the excess alcohol or alcohol and solvent by, for example, evaporation. Evaporation may be carried out under a vacuum at elevated temperature.

An ester of the compound of formula (I) may be used to prepare an ester of a compound of formula (VII), which are also disclosed in U.K. Patent Specification Nos. 1 603 208 and 1 594 934:

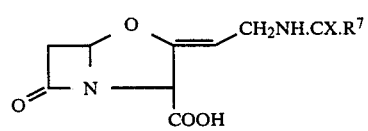   (VII)

wherein $R^7$ is selected from hydrogen, an aliphatic group, a cycloaliphatic group, an aryl or a C-attached heterocyclic group, by reaction with a carboxylic acid of formula (VIII):

   (VIII)

wherein $R^7$ is as defined in relation to formula (VII) and X and $X^1$ are each independently selected from O and S.

Suitable $R^7$ groups are optionally substituted $C_{1-6}$ alkyl, $C_{2-6}$ alkenyl, $C_{3-6}$ cycloalkyl, aryl($C_{1-6}$)alkyl and aryl groups.

Suitably the alkyl group or the alkyl moiety in the aralkyl group contains up to 4 carbon atoms and is unsubsitututed or substituted by up to 3 halogen atoms or by hydroxy (but not $C_1$ hydroxy). Suitable aryl groups or aryl moieties in the aralkyl group are phenyl or phenyl substituted by one or two groups selected from $C_{1-6}$ alkyl, $C_{1-6}$ alkoxy, fluorine or chlorine.

A preferred aryl($C_{1-6}$)alkyl group is benzyl.

Suitable heterocyclic groups include single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$) alkyl, aryl or oxo groups.

Preferably $R^7$ is hydrogen.

This reaction, which proceeds via the formation of an ester of a mixed anhydride of formula (IX):

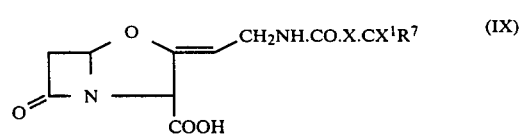   (IX)

(wherein $R^7$, X and $X^1$ are as defined in relation to formula (VII), may be catalysed by the presence of an amine.

An ester of the compound of formula (I) may be used to prepare an ester of the compound of formula (X) which is disclosed in U.K. patent specification Nos. 1 603 208 and 1 585 124;

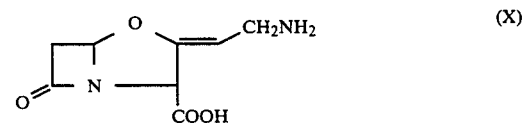   (X)

by reaction with equimolar amounts of water.

In each of the above reactions, an ester (such as the sub-formula (b) ester e.g. the benzyl ester) of formula (I) is used to prepare the corresponding ester of the compounds of formula (V), (VII) and (X) and the ester so prepared may then be converted to the desired compound (i.e. the salt, ester or free acid of the compound of formula (V), (VII) or (X)) by the usual methods.

This invention will now be illustrated with reference to the following Examples. (All temperatures listed herein are in degrees Centigrade).

EXAMPLE 1

Preparation of Benzyl 9-isocyanatodeoxyclavulanate

Benzyl clavulanate (1.5 g) in toluene (10 ml) was stirred and triphenylphosphine (1.6 g) was added. When all was dissolved, the solution was cooled to $-20°$ and a solution of cyanic acid in toluene (70 ml, 0.1M solution) was added. The mixture was cooled to −40° and then diethyl azodicarboxylate (1.1 ml) added. The mixture was allowed to warm to ambient temperature. It was then partially evaporated under reduced pressure and subjected to elution chromatography on silica gel using hexane:ethyl acetate (3:1). The isocyanate eluted before a trace of diene. Fractions containing the desired compound (by t.l.c.) were combined and evaporated to an oil. This has i.r. spectrum (film) absorption peaks at 2260, 1800, 1760, 1705 and 700 cm (and others); yield 0.15 g.

EXAMPLE 2

Preparation of Benzyl 9-isocyanatodeoxyclavulanate

Powdered sodium cyanate (15 g) was suspended in water (75 ml) and toluene (300 ml) added. The mixture was stirred vigorously and cooled to −50°. 5N sulphuric acid (50 ml) was added while maintaining the temperature at or below 0°. After a further 1 minute, stirring was stopped, and the toluene layer was decanted off and filtered through phase separating paper.

Benzyl clavulanate (4 g) and triphenylphosphine (4.35 g) were dissolved in distilled tetrahydrofuran (20 ml) and the stirred solution was cooled to −10° and treated with 250 ml of the above prepared toluene solution. When the mixture had reached −10°, diethylazodicarboxylate (2.73 ml) was added. The mixture was stirred for 15 minutes, stored for 1 hour in a refrigerator, then evaporated under reduced pressure to approximately 20 ml and applied to a silica column. It was chromatographed rapidly, eluting with ethyl acetate:-hexane (1:2). Fractions containing benzyl 9-isocyanato-9-deoxy clavulanate were combined and evaporated under reduced pressure.

EXAMPLE A

Use of Benzyl 9-isocyanatodeoxyclavulanate to prepare Benzyl 9-benzyloxycarbonylaminodeoxyclavulanate Benzyl 9-isocyanatodeoxyclavulanate (prepared in Example 1) was dissolved in excess benzyl alcohol (ca. 20 ml) and allowed to remain at ambient temperature overnight. Most of the benzyl alcohol was evaporated under a high vacuum at about 50°. The residue slowly crystallised. Then carbon tetrachloride (a few drops) was added, the temperature was reduced to −10° and the liquid was removed with a pipette. The residue was then dried in vacuo.

EXAMPLE B

Use of Benzyl 9-isocyanato-9-deoxy clavulanate to prepare Benzyl
9-(2'-trimethylsilylethoxycarbonylamino)-9-deoxy-clavulanate The residue prepared in Example 2 was immediately dissolved in ethyl acetate (5 ml) and treated with 2-trimethylsilylethanol (2.2 ml). The solution was kept for 20 hours at room temperature and for a further 4 hours at 55<. The solvents were then removed under reduced pressure (with a high vacuum to remove 2-trimethyl-silylethanol) and the residue was chromatographed on silica, eluting with ethyl acetate:hexane (1:2). Appropriate fractions were combined and evaporated to provide benzyl 9-(2'-trimethylsilylethoxycarbonylamino)-9-deoxyclavulanate (2.03 g) as a pale yellow oil). $\nu_{max}$ (CHCl$_3$) 3450, 1800, 1745, 1710, 1500 cm$^{-1}$. (CDCl$_3$) 0.95 (2H, t, J 8.5 Hz), 3.01 (1H, d, J 17 Hz), 3.45 (1H, dd, J 17 and 2.5 Hz), 3.79 (2H, t, J 7 Hz), 4.13 (2H, t, J 8.5 Hz), 4.4–4.8 (2H, m), 5.03 (1H, s), 5.17 (2H, s), 5.65 (1H, d, J 2.5 Hz), 7.33 (5H, s).

EXAMPLE C

Use of benzyl 9-isocyanato-9-deoxy clavulanate to prepare benzyl 9-formamido-9-deoxy clavulanate Crude benzyl 9-isocyanato-9-deoxyclavulanate (prepared as in Example 2, but not chromatographed) was dissolved in dichloromethane (50 ml) and stirred at room temperature. The solution was treated with pyridine (2.26 ml) and formic acid (1.04 ml) and stirred for 2 hours. It was then diluted with dichloromethane (50 ml), washed with 0.5N hydrochloric acid (100 ml), water (100 ml) and 1N sodium bicarbonate solution (100 ml), dried over anhydrous MgSO$_4$ and evaporated under reduced pressure. The residue was chromatographed on silica, eluting with ethyl acetate/hexane 1:1 (until most of the triphenylphosphine oxide had been removed), then with ethyl acetate/hexane 4:1 (until the required compound began to elute from the column) and finally with ethyl acetate. Appropriate fractions were combined and evaporated under reduced pressure. The residue was rechromatographed as above to provide an oil, which solidified on desiccation to yield benzyl 9-formamido-9-deoxyclavulanate as an off-white solid (2.2 g). $\nu_{max}$(CHCl$_3$) 3450, 1805, 1750, 1685 and 1500 cm$^{-1}$.

I claim:

1. A compound of formula I

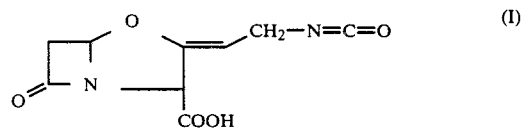

or a salt of a carboxylic acid or ester thereof.

2. A compound according to claim 1 comprising an ester of formula I.

3. A compound according to claim 2 wherein the ester group is of sub-formula (a), (b), (c), (d), (e) or (f):

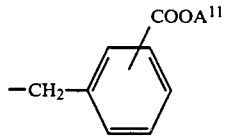 (f)

wherein:

$A^1$ is a hydrogen atom, $C_{1-6}$ alkanoyl or a $C_{1-5}$ alkyl group optionally substituted by a $C_{1-7}$ alkoxy or $C_{1-7}$ carboxylic acyloxy, or an alkenyl or alkynyl group of up to 5 carbon atoms;

$A^2$ is a hydrogen atom or a methyl group; or CHA$^1$A$^2$ is a phenacyl or bromophenacyl group;

$A^3$ is a phenyl group, or a phenyl group substituted by a fluorine, chlorine or bromine atom or a nitro, $C_{1-3}$ alkyl or $C_{1-3}$ alkoxy group;

$A^4$ is a hydrogen atom or a phenyl group, or a phenyl group substituted by a fluorine, chlorine or bromine atom or a nitro, $C_{1-3}$ alkyl or $C_{1-3}$ alkoxy group;

$A^5$ is a hydrogen atom or a methyl group;

$A^6$ is a $C_{1-4}$ alkyl, phenyl or $C_{1-4}$ alkoxy group, or $A^5$ is joined to $A^6$ such that subformula (c) forms a phthalidyl, dimethyl-phthalidyl or dimethoxyphthalidyl group;

$A^7$ is a $C_{1-4}$ alkyl, phenyl, chlorophenyl or nitro-phenyl group;

$A^8$ is a $C_{1-4}$ alkyl or phenyl group;

$A^9$ is a $C_{1-4}$ alkyl or phenyl group;

$A^{10}$ is a $C_{1-4}$ alkyl; and $A^{11}$ is $C_{1-4}$ alkyl.

4. Benzyl 9-isocyanatodeoxyclavulanate.

* * * * *